US006846495B2

(12) United States Patent
Dobrozsi et al.

(10) Patent No.: US 6,846,495 B2
(45) Date of Patent: \*Jan. 25, 2005

(54) COMPOSITIONS HAVING IMPROVED DELIVERY OF ACTIVES

(75) Inventors: Douglas Joseph Dobrozsi, Loveland, OH (US); Jerry William Hayes, II, Cincinnati, OH (US); Kishor Jivanlal Desai, West Chester, OH (US); Brian James Robbins, Staines (GB)

(73) Assignee: The Procter & Gamble Company, Cincinnati, OH (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/466,950

(22) Filed: Dec. 20, 1999

(65) Prior Publication Data

US 2003/0139437 A1 Jul. 24, 2003

Related U.S. Application Data

(60) Provisional application No. 60/115,378, filed on Jan. 11, 1999.

(51) Int. Cl.$^7$ .......................... A61K 47/00; A61K 9/68; A61K 9/66; A61K 9/64; A61K 9/14
(52) U.S. Cl. ........................ 424/439; 424/48; 424/400; 424/440; 424/441; 424/451; 424/452; 424/455; 424/456; 424/464; 424/465; 424/484; 424/489
(58) Field of Search ................................. 424/400, 439, 424/440, 441, 451, 452, 455, 456, 464, 465, 484, 489, 48

(56) References Cited

U.S. PATENT DOCUMENTS

| | | | |
|---|---|---|---|
| 3,085,942 A | * 4/1963 | Magid et al. | 514/289 |
| 4,032,661 A | 6/1977 | Rowsell et al. | 424/337 |
| 4,136,163 A | 1/1979 | Watson et al. | 424/54 |
| 4,232,002 A | 11/1980 | Nogrady | 424/45 |
| 4,459,425 A | 7/1984 | Amano et al. | 568/666 |
| 4,474,752 A | 10/1984 | Haslam et al. | 424/78 |
| 4,474,985 A | 10/1984 | Keel et al. | 564/216 |
| 4,478,822 A | 10/1984 | Haslam et al. | 424/78 |
| 4,839,176 A | 6/1989 | Pankhania et al. | 424/465 |
| 4,883,660 A | * 11/1989 | Blackman et al. | 424/434 |
| 5,100,898 A | 3/1992 | Sorrentino | 514/281 |
| 5,196,436 A | 3/1993 | Smith | 514/289 |
| 5,196,486 A | 3/1993 | Stephenson | 525/328.8 |
| 5,458,879 A | 10/1995 | Singh et al. | 424/400 |
| 5,846,557 A | * 12/1998 | Eisenstadt et al. | 424/439 |
| 5,955,098 A | 9/1999 | Dugger, III | 424/435 |
| 6,027,746 A | * 2/2000 | Lech | 424/455 |
| 6,110,486 A | 8/2000 | Dugger, III | 424/435 |
| 6,335,030 B1 | * 1/2002 | Hoeck et al. | 424/443 |

FOREIGN PATENT DOCUMENTS

| | | | |
|---|---|---|---|
| EP | 0295941 A2 | 12/1988 | A61K/9/10 |
| WO | WO 93/00072 | 1/1993 | A61K/9/48 |
| WO | WO 94/18970 | 9/1994 | A61K/31/44 |
| WO | WO 95/04527 | 2/1995 | A61K/31/165 |
| WO | WO 95/19759 | 7/1995 | A61K/47/10 |
| WO | WO 95/23595 | 9/1995 | A61K/9/48 |
| WO | WO 96/23486 | 8/1996 | A61K/9/00 |
| WO | WO 98/52545 | 11/1998 | A61K/9/20 |
| WO | WO 99/16417 | 4/1999 | A61K/9/00 |

OTHER PUBLICATIONS

Lund, "Stability of Medicinal Products", *The Pharmaceutical Codex*, pp. 277–310, Editor: W. Lund, 12$^{th}$ Edition, The Pharmaceutical Press, London (1994).

Harris et al., "Drug Deliver Via the Mucous Membranes of the Oral Cavity", *J. of Pharmaceutical Sciences*, vol. 81, No. 1, pp. 1–10 (1992).

Char et al., "Nasal Deliver of [$^{14}$C]Dextromethorphan Hydrochloride in Rats: Levels in Plasma and Brain", *J. of Pharmaceutical Sciences*, vol. 81, No. 8, pp. 750–752 (1992).

Martin et al., "Physical Chemical Principles in the Pharmaceutical Sciences", *Physical Pharmacy*, p. 237, Editor: G. H. Mundorff, 4$^{th}$ Edition, Lea & Febiger, Philadelphia, London (1993).

Wells, "Drug Stability", *Pharmaceutical Preformulations: The Physicochemical Properties of Drug Substances*, pp. 168–172, John Wiley & Sons, NY (1988).

Hoffman et al., "Catecholamides, Sympathomimetic Drugs, and Adrenergic Receptor Antagonists", *Goodman & Gilman's The Pharmacological Basis of Therapeutics*, Chapter 10, pp. 221–224, 9$^{th}$ Edition, McGraw–Hill (1996).

Catterall et al., "Local Anesthetics", *Goodman & Gilman's The Pharmacological Basis of Therapeutics*, Chapter 15, pp. 331–347, 9$^{th}$ Edition, McGraw–Hill (1996).

Reisine et al., "Opioid Analgesics and Antagonists", *Goodman & Gilman's The Pharmacological Basis of Therapeutics*, Chapter 23, pp. 551–552, 9$^{th}$ Edition, McGraw–Hill (1996).

(List continued on next page.)

Primary Examiner—Shelley A. Dodson
(74) Attorney, Agent, or Firm—Joan B. Cunningham; John M. Howell

(57) ABSTRACT

The present invention pertains to compositions having improved delivery of pharmaceutical actives. These compositions comprise pharmaceutical actives in an anhydrous solvent. These compositions may take the form of liquid elixirs placed into the mouth and eventually swallowed, or can be delivered via liquid-filled drops, metered liquid dosing devices, atomizers and liquid-releasing, edible capsules.

16 Claims, No Drawings

OTHER PUBLICATIONS

Babe et al., "Histamine, Bradykinin, and Their Antagonists", *Goodman & Gilman's The Pharmacological Basis of Therapeutics*, Chapter 25, pp. 581–600, 9th Edition, McGraw–Hill (1996).

Insel, "Analgesic–Antipyretic and Antiinflammatory Agents and Drugs Employed in the Treatment of Gout", *Goodman & Gilman's The Pharmacological Basis of Therapeutics*, Chapter 27, pp. 617–657, 9th Edition, McGraw–Hill (1996).

"Iodides" pp. 252–253, *Drugs in Bronchial Mucology*, Eds. P. C. Braga, M.D. and L. Allegra, M.D., Raven Press, NY (1989).

"Sol–Layer and Mucus Hydration" pp. 309–312, *Drugs in Bronchial Mucology*, Eds. P. C. Braga, M.D. and L. Allegra, M.D., Raven Press, NY (1989).

Rote Liste, No. 23140, "Bisolvon–Linctus cough syrup", (with translation by Ralph McElroy Translation Co.) (1994).

* cited by examiner

US 6,846,495 B2

COMPOSITIONS HAVING IMPROVED DELIVERY OF ACTIVES

This application claims the benefit of Provisional Application No. 60/115,378, filed Jan. 11, 1999.

TECHNICAL FIELD

The present invention pertains to compositions having improved delivery of pharmaceutical active ingredients. These compositions comprise pharmaceutical actives in an anhydrous, hydrophilic solvent. These compositions may take the form of liquid elixirs placed into the mouth and eventually swallowed, or can be delivered via liquid-filled lozenges and gums, metered liquid dosing devices, atomizers and liquid-releasing, edible capsules. Such compositions are particularly useful for treating symptoms associated with respiratory illnesses.

BACKGROUND OF THE INVENTION

Routes for delivering pharmaceutical actives include delivering actives by intranasal, pulmonary, buccal, sublingual, transdermal, and rectal administration. These routes tend to be used for avoiding first-pass metabolism of drugs that are swallowed. "First past metabolism" refers to the arrangement and order of placement of the metabolizing enzymes within the body of a human, with respect to the path followed by substances that enter the gastrointestinal tract by swallowing, and are absorbed into the general blood circulation. Items swallowed by humans, including food, drink, and medicines, enter the stomach and from there flow into the intestine. Many of the chemicals associated with the food, drink, or medicine pass through the mucosal membranes in the gastrointestinal tract and into the blood in the mesenteric veins draining from the intestine. The blood flow from the mesenteric veins passes into the liver. Metabolizing enzymes in the mucosal membranes of the intestine and in the liver can chemically alter the nature of substances passing from the intestine, through the liver, and into the common blood circulation of the body. Since all swallowed medicines are subject to the metabolizing capacity of the intestinal mucosal membranes and the liver before entering the general blood circulation of the body, frequently only a small fraction of those substances go unmetabolized, and reach the general blood circulation Avoiding first pass metabolism can increase the bioavailability, or blood concentrations of the administered compound. Metabolic formation of metabolites of the administered compound, however, can at the same time decrease. Where formation of metabolites from the first pass metabolism is desirable, avoiding the first pass metabolism is not preferred since it logically leads to lower amounts of the metabolite in the blood. Furthermore, the blood concentrations of the active substance can increase, leading to potential toxicity or side effects attributable to the active per se. Reducing the amount of active in the dose for avoiding toxicity, concomitantly decreases the circulating blood levels of the active metabolite. This results in loss of therapeutic affect and ultimately, benefit to the patient. In order to provide a medication that is effective and avoids unwanted side effects, the composition and its means of delivery must be modified.

Respiratory illnesses covers a broad range of ailments, including viral infections and allergic reaction to inhaled allergens. Viral infections in the upper respiratory tract of humans leads to illness usually referred to as colds, or influenza. Such an illness is quite common in the general population and can be the cause of significant discomfort and suffering. Allergen inhalation also negatively impacts a fair number in the population at the same or even at a greater degree than those having a viral infection.

There are no generally regarded effective and convenient methods for preventing viral infections or allergies. In the case of viral infections, the body's natural defense mechanisms fight the infection for a period of time normally ranging from 3 days to 2 weeks. This being the case, the most commonly employed medicines treat the uncomfortable, problematic symptoms of these respiratory ailments. These symptoms include stuffy and runny noses, soreness and inflammation in the nose and throat, fits of coughing, general aches in the body, fever, and headache. Of these symptoms, coughing in uncontrollable fits is considered by many to be the most problematic and uncomfortable. Coughing disrupts normal respiration, leading to increased headache and sore throat as well as loss of sleep to the sufferer and others living with the sufferer The compositions used to treat the above mentioned symptoms generally fall into one of the following pharmacological classifications: antihistamines; decongestants; antitussives; expectorants; mucolytics; analgesics, antipyretic and anti-inflammatory agents. The compositions are manufactured in a number of product forms, the most common being liquid syrups and elixirs for swallowing, mouth drops and lozenges as well as inhalants and topical creams or lotions that release volatile agents that are inhaled through the nose into respiratory tract. The compositions are typically swallowed immediately, or slowly dissolved in the mouth. They typically contain actives such as guaifenesin, that aids the body in the removal of excess respiratory mucus or phlegm, diphenhydramine, that lessens the negative effects including coughing and other symptoms due to histamine produced in the body in response to the viral infection, and dextromethorphan, that acts within the part of the human brain controlling the coughing reflex. Among these actives, dextromethorphan is the most commonly used active in the world for relief of cough.

Dextromethorphan, by virtue of it's physicochemical, absorption, and bioavailability properties, is a very good candidate for increasing bioavailability via methods of administration other than swallowing. For example it has been reported in patents and pharmaceutical literature that substantial increases in bioavailability can be achieved using intranasal formulations; see H. Char et al, *Nasal Delivery of 14-C Dextromethorphan in Rats*, Journal of Pharmaceutical Sciences 81:750, 1992.

What has not been realized until now is that after careful and diligent research into pharmaceutic, therapeutic, and side effect properties of active compounds, compositions can be made to positively improve the therapeutic effect without increased side effects or toxicity.

SUMMARY OF THE INVENTION

An object, therefore, of the present invention is to provide improved compositions for treating the symptoms associated with respiratory ailments, particularly minimizing fits of coughing. The compositions are solutions of pharmaceutical actives in small volumes of anhydrous, hydrophilic liquids providing rapid delivery of pharmaceutical actives including antitussives; antihistamines (including non-sedating antihistamines); decongestants; expectorants; mucolytics; analgesic, antipyretic and anti-inflammatory agents and local anesthetics for treating the symptoms of respiratory illnesses. The compositions can be dosed using a variety of product forms and, or package delivery options. The compositions of the present invention provide improved activity while minimizing potential side effects of the pharmaceutical active. It is also an objective of the subject invention to provide methods for achieving rapid transmucosal delivery of the aforementioned compositions.

Definitions and Terms

The following are definitions of terms found in the present specification:

1. Transmucosal Delivery:

Refers to application of drugs to the mucosal membranes of the oral cavity, including buccal (cheek), lips, gums, palates, and tongue, with the goal of the drug passing through the skin covering these places and entering the bloodstream.

2. Therapeutic Dose

Refers to the amount of the substance that when administered to a person in the proper form, will produce the desired effect within the body with minimal undesired side.

3. Pharmaceutical Active/Active:

Refers to the chemical molecule which exerts the desired effect on the body, when administered in the proper amount and form.

4. Active Metabolites

Refers to the chemical species of the pharmaceutical active upon the active undergoing metabolism.

5. Monomolecular Dispersion

Refers to the fact that molecules of the active are free and unencumbered from diffusion by association in crystalline or amorphous solid forms, or poly molecular association.

6. Percent Solubility Value

Refers to the equilibrium solubility limit or maximum solubility of a molecule in a solvent at usual room temperature, expressed as the weight percent of the molecule in the composition.

DETAILED DESCRIPTION OF THE INVENTION

The compositions of the present invention comprise pharmaceutical actives referred to herein as "actives" for treating illnesses, particularly symptoms associated with respiratory ailments such as colds, influenza as well as allergy. These actives are most frequently used for treating the most problematic symptoms including a stuffy and runny nose, soreness and inflammation in the nose and throat, fits of coughing, general aches in the body, fever, and headache. In the present invention, when actives are combined with small volumes of anhydrous solvents, the actives obtain enhanced transmucosal delivery into the blood In the case that active metabolites contribute to the desired therapeutic effect, this enhanced delivery is achieved without appreciably lowering the level of the corresponding active metabolites. Furthermore, the level of active in the blood is maintained at a level that avoids unwanted side effects brought on by too high of levels of active in the blood.

The composition comprises a pharmaceutical active in an hydrophilic, water-miscible, anhydrous solvent wherein the pharmaceutical active in its un-ionized form has a percent solubility value in the solvent at ambient temperature that is equal to or greater than 0.075% and the pharmaceutical active is in its free, un-ionized form as a monomolecular dispersion in the solvent.

The pharmaceutical active of the present invention has a molecular weight of less than 500 grams per mole, is capable of being ionized when in an aqueous solvent and has an octanol-water partition coefficient when in the un-ionized form of at least 100. The octanol-water partition coefficient is disclosed in A. Martin, P. Bustamante, and A. H. C. Chun, *Physical Pharmacy*, Fourth Edition, Lea and Febiger publishers, Philadelphia, 1993, page 237; herein incorporated by reference.

The actives that comprise compositions of the present invention fall into at least one of the following pharmacological classifications: antitussives; antihistamines; non-sedating antihistamines; decongestants; expectorants; mucolytics, analgesic, antipyretic anti-inflammatory agents, local anesthetics and mixtures thereof. References that describe the use of such actives include J. G. Hardman, *The Pharmacologic Basis of Therapeutics*, Ninth Edition, McGraw-Hill, New York, 1995. Antitussives useful in the present invention include, but, are not restricted to the group consisting of codeine, dextromethorphan, dextrorphan, diphenhydramine, hydrocodone, noscapine, oxycodone, pentoxyverine and mixtures thereof. Antihistamines useful in the present invention include, but, are not restricted to the group consisting of acrivastine, azatadine, brompheniramine, chlorpheniramine, clemastine, cyproheptadine, dexbrompheniramine, dimenhydrinate, diphenhydramine, doxylamine, hydroxyzine, meclizine, phenindamine, phenyltoloxamine, promethazine, pyrilamine, tripelennamine, triprolidine and mixtures thereof. Non-sedating antihistamines useful in the present invention include, but, are not restricted to the group consisting of astemizole, cetirizine, ebastine, fexofenadine, loratidine, terfenadine, and mixtures thereof. Decongestants useful in the present invention include, but, are not restricted to the group consisting of phenylpropanolamine, pseudoephedrine, ephedrine, phenylephrine, oxymetazoline, and mixtures thereof Expectorants useful in the present invention include, but, are not restricted to the group consisting of ammonium chloride, guaifenesin, ipecac fluid extract, potassium iodide and mixtures thereof. Mucolytics useful in the present invention include, but, are not restricted to the group consisting of acetylcycsteine, ambroxol, bromhexine and mixtures thereof. Analgesic, antipyretic and anti-inflammatory agents useful in the present invention include, but, are not restricted to the group consisting of acetaminophen, aspirin, diclofenac, diflunisal, etodolac, fenoprofen, flurbiprofen, ibuprofen, ketoprofen, ketorolac, nabumetone, naproxen, piroxicam, caffeine and mixtures thereof. Local anesthetics useful in the present invention include, but, are not restricted to the group consisting of lidocaine, benzocaine, phenol, dyclonine, benzonotate and mixtures thereof.

Actives in compositions of the present invention are soluble in the anhydrous solvent. The concentration of actives in the solvent is preferably less than or equal to 125% of the percent solubility value, more preferably less than or equal to the percent solubility value of the pharmaceutical active. To maximize the benefits of the compositions of the present invention, the active is preferably in solution as monomolecular dispersion. The actives useful in the present invention are present in the solvent system at a level from about 0.075% to about 25.0%, preferably from about 0.28% to 10.0% by weight of the composition.

It is preferred that the active is in it free form, however the salt form of the active is also useful in the present invention. Regardless of its form, the active is in its un-ionized state in the monomolecular dispersion in said solvent system.

Actives of particularly use are those that arrest uncontrollable fits coughing. Of the antitussives available, dextromethorphan is preferred. Dextromethorphan is known to have pharmacological activity as an antitussive agent and is described in U.S. Pat. No. 5,196,436, Smith; incorporated herein by reference. As used herein, "dextromethorphan" means racemethorphan, 3-methoxy-17-methylmorphinan (dl-cis-1,3,4,9,10,10a-hexahydro-6-methoxy-11-methyl-2H-10,4a-iminoethanophenanthrene and pharmaceutically-acceptable salts thereof. Compositions of the present comprising dextromethorphan preferably comprise from about 0.1% to about 9.3%, more preferably from about 0.26% to about 6.2% and most preferably from about 1.16% to about 4.6% dextromethorphan. Other safe and effective amounts of other cough/cold drug actives may be included in such dextromethorphan-containing compositions.

In the composition of the present invention to the user, dose level of dextromethorphan delivered to the consumer is from about 6.85 milligrams to about 30.83 milligrams per dose. In the case where the hydrobromide monohydrate salt of dextromethorphan is in the composition, the dose level of the hydrobromide monohydrate salt of dextromethorphan delivered to the consumer is from about 10.0 milligrams to about 45 milligrams per dose.

The un-ionized form of the pharmaceutical active is maintained using an anhydrous solvent. By anhydrous it is meant that the solvent contains less than about 5% water. The anhydrous solvent of the present invention comprises from about 60% to about 99.975%, preferably from 70% to about 99% and most preferably from about 85% to about 98% by weight of the composition.

The anhydrous solvent of the present invention is normally liquid at ambient or room temperatures. It is water-soluble or water-miscible. The solvents are selected from the group consisting propylene glycol, ethanol, poly(ethylene glycol) or PEG, propylene carbonate, diethylene glycol monoethyl ether, poloxamer, glycofurol, glycerol, and mixtures thereof. There are mixtures of these solvents that are particularly preferred for certain product forms of the present invention. For example, if the product form is an elixir, liquid capsule or liquid containing lozenge, the solvent is a combination of propylene glycol, ethanol, and PEG. If the product form is a spray, the solvents is a combination of propylene glycol, ethanol, PEG and usually propylene carbonate. The level of each solvent that makes up these mixtures is partially dependent on aesthetic benefits sought by the formulator.

Optional Ingredients

Ingredients normally associated with cold and influenza treatment medicines can be used with the pharmaceutical actives disclosed herein. Such ingredients are disclosed in U.S. Pat. No. 5,196,436, incorporated herein by reference. Additionally, the following ingredients may be used in the present invention:

Buffers and mixtures of buffering agents, including basic buffers as single components with pKa of from 8 to 11, include triethanolamine, salts of amino acids, including alkaline salts of glycine, glycylglycine, glutamine or other amino acids, alkaline salts of phosphate, carbonate and mixtures thereof. The buffers provide compositional resistance to pH changes upon dilution of the composition with saliva within the range of 7 to 10, preferably 8 to 10.

Sweeteners, including aspartame, saccharin and its salts, Sucralose™ (sold by the McNeil Specialty Products Co., New Brunswick, N.J.); Prosweet™ (sold by the Virginia Dare Extract Co., New York, N.Y.); Magnasweet™ (sold by MAFCO Worldwide Corp., Licorice Division, Camden, N.J.); ammonium glycyrrhizinate, its salts, Talin™ (Thaumatin) and its diluted products, such as Talin GA90, (sold by the Talin Food Company, Birkenhead, England); and Acesulfame K, and mixtures thereof.

Flavorants, include anise, oil of peppermint, oil of clove, eucalyptus, lemon, lime, honey lemon, red fruit, mint, grapefruit, orange, cherry cola and mixtures thereof.

Sensory agents. Also useful herein are sensory agents selected from the group consisting of coolants, salivating agents, warming agents. Preferably these agents are present in the compositions at a level of from about 0.001% to about 10%, preferably from about 0.1% to about 1%, by weight of the composition.

Suitable cooling agents include carboxamides, menthols, thymol, camphor, capsicum, phenol, eucalyptus oil, benzyl alcohol, salicyl alcohol, ethanol, clove bud oil, and hexylresorcinol, ketals, diols, and mixtures thereof. Preferred coolants are the paramenthan carboxyamide agents such as N-ethyl-p-menthan-3-carboxamide (WS-3 supplied by Sterling Organics), taught by U.S. Pat. No. 4,136,163, issued Jan. 23, 1979, to Watson et al., which is incorporated herein by reference in its entirety. Another preferred paramenthan carboxyamide agent is N,2,3-trimethyl-2-isopropylbutanamide, known as "WS-23", and mixtures of WS-3 and WS-23.

Additional preferred coolants are selected from the group consisting of menthol, 3-1-menthoxypropane-1,2-diol, known as TK-10 supplied by Takasago Perfumery Co., Ltd., Tokyo, Japan, menthone glycerol acetal known as MGA, manufactured by Haarmann and Reimer, menthyl lactate known as Frescolatg manufactured by Haarmann and Reimer, and mixtures thereof.

Additonal cooling agents include cyclic sulphones and sulphoxides and others, all of which are described in U.S. Pat. No. 4,032,661, issued Jun. 28, 1977, to Rowsell et al., which is herein incorporated by reference.

The terms "menthol" and "menthyl" as used herein include dextro- and levoratotory isomers of these compounds and racemic mixtures thereof.

TK-10 is described in detail in U.S. Pat. No. 4,459,425, issued Jul. 10, 1984 to Amano et al. and incorporated herein by reference.

Salivating agents of the present invention include Jambu® manufactured by Takasago Perfumery Co., Ltd., Tokyo, Japan.

Warming agents include capsicum and nicotinate esters, such as benzyl nicotinate.

Method of Use

In terms of the methods of delivery of the active, it is generally accepted that oral mucosal delivery inside the mouth must be targeted to the sub-lingual region in order to achieve a very rapid therapeutic effect; see D. Harris and J. R. Robinson, *Drug Delivery via the Mucus Membranes of the Oral Cavity*, Journal of Pharmaceutical Sciences 81: 1, 1992. Such dosage forms are designed to be placed under the tongue, on the floor of the mouth, and held there for some extended time. The inventors have found, however, that a large increase in bioavailability with very rapid absorption can be achieved when the subject compositions are placed against any of the mucosal membranes of the mouth, even onto the tongue and swallowed. The form of the invention is a liquid elixir solution. It is intended to be applied to any of the mucosal membranes within the mouth. This can be achieved using a medicine dropper that is calibrated to indicate the proper amount to be administered, and squirting the elixir onto the tongue prior to swallowing. The elixir can be atomized into mouth and throat and then swallowed. It can be encapsulated into some sort of shell which makes it portable and convenient to transport and administer without having to measure the quantity of liquid elixir. Examples of encapsulation shells include hard candies as are used for lozenges, chewing gums, gelatin, or non-gelatin (e.g. starch-based) shells. The elixir may be packaged into a small, disposable vial which can readily be opened and squirted into the mouth, the entire vial containing exactly one therapeutic dose. Typical dosage forms of the composition of the present invention contain no more than about 3 ml., preferable from about 0.2 ml. to about 3 ml.

One preferred form is to encapsulate the liquid into a shell of hard candy or gelatin. The shell containing substances to pretreat the mucosa and thereby enhance the absorption of the active from the liquid center. The pretreatment occurs by sucking or chewing the shell material, and the advantage is gained by separating in time the treatment of the mucosa, which occurs first, followed by the presentation of the active to be absorbed. Examples of substances for pretreatment of the mucosal membranes are membrane penetration enhancers that are commonly known in the art, examples including menthol, peppermint oil, surfactants such as polysorbate 80 or poloxamer. Another example of a mucosal membrane pretreatment are buffers as listed above, which would precondition salivary micro environment pH in the range of 8 to 10.

EXAMPLES

Example I

Liquid Elixir

| Item # | Material | % Comp. (w/w) |
|---|---|---|
| 1 | Dextromethorphan Base | 2.055 |
| 2 | Ethanol (100%) | 10.000 |
| 3 | Polyethylene Glycol 600 | 81.88 |
| 4 | Propylene Glycol | 5.000 |
| 5 | Sodium Saccharin | 0.300 |
| 6 | Pro-Sweet Liquid K | 0.700 |
| 7 | Monoammonium Glycyrrhizinate | 0.050 |
| 8 | Anethole | 0.0075 |
| 9 | Green Shade | 0.003 |
|  | Total | 100.000 |

Add a portion of Ethanol to the active (Dextromethorphan Base) and solid sweetening agents (Sucralose, Monoammonium Glycyrrizinate) and continuously mix at low heat (30° C.). To this vessel add the additional solvents (Propylene Glycol, Polyethylene Glycol 600) and liquid sweeteners (Pro-sweet Liquid K). Mix until all materials are in solution, about 2 hours time. Prepare a premix of flavorants and colorants in the remaining portion of ethanol, and add to the vessel containing the nearly completed solution. Mix until a homogenous solution is obtained, and filter through a US # 100 mesh sieve (product density=1.07 g/ml.). Fill into amber glass bottles, and cap with an integrated cap/calibrated medicine dropper assembly.

About 1.0 ml. of the elixir dropped onto the tongue and then swallowed. Dextromethorphan is rapidly absorbed into the blood.

Example II

Liquid Elixir

| Item # | Material | % Comp. (w/w) |
|---|---|---|
| 1 | Dextromethorphan Base | 2.055 |
| 2 | Ethanol (100%) | 10.000 |
| 3 | Polyethylene Glycol 600 | 78.285 |
| 4 | Propylene Glycol | 5.000 |
| 5 | Triethanolamine | 3.740 |
| 6 | Sucralose | 0.150 |
| 7 | Pro-Sweet Liquid K | 0.700 |
| 8 | Monoammonium Glycyrrhizinate | 0.050 |
| 9 | Flavorant | 0.015 |
| 10 | Colorant | 0.005 |
|  | Total | 100.000 |

Add a portion of Ethanol to the active (Dextromethorphan Base) and solid sweetening agents (Sucralose, Monoammonium Glycyrrizinate) and continuously mixed at low heat (30° C.). To this vessel add the additional solvents (Propylene Glycol, Polyethylene Glycol 600), liquid sweeteners (Pro-sweet Liquid K), and buffer (Triethanolamine, a liquid). Mix until all materials are in solution, about 2 hours time. Prepare a premix of flavorants and colorants in the remaining portion of ethanol, and add to the vessel containing the nearly completed solution. Mix until a homogenous solution is obtained, and filter through a US # 100 mesh sieve (product density=1.07 g/ml.). Fill into amber glass bottles, and cap with an integrated cap/calibrated medicine dropper assembly.

About 1.0 ml. of the elixir dropped onto the tongue and then swallowed. Dextromethorphan is rapidly absorbed into the blood.

Example III

Liquid Spray

| Item # | Material | % Comp. (w/w) |
|---|---|---|
| 1 | Dextromethorphan Base | 3.425 |
| 2 | Ethanol (100%) | 5.350 |
| 3 | Polyethylene Glycol 400 | 50.155 |
| 4 | Propylene Carbonate | 40.000 |
| 5 | Sucralose | 0.300 |
| 6 | Pro-Sweet Liquid K | 0.700 |
| 7 | Monoammonium Glycyrrhizinate | 0.050 |
| 8 | Flavorant | 0.015 |
| 9 | Green Shade CSL-15689* | 0.005 |
|  | Total | 100.000 |

*obtained from the Warner Jenkins Co., St. Louis, MO, USA.

Add a portion of Ethanol to the active (Dextromethorphan Base) and solid sweetening agents (Sucralose, Monoammonium Glycyrrizinate) and continuously mixed at low heat (30° C.). To this vessel add the additional solvents (Propylene Carbonate, Polyethylene Glycol 400) and liquid sweeteners (Pro-sweet Liquid K). Mix until all materials are in solution, about 2 hours time. Prepare a premix of flavorants and colorants in the remaining portion of ethanol, and add to the vessel containing the nearly completed solution. Mix until a homogenous solution is obtained, and filter through a US # 100 mesh sieve (product density=1.075 g/ml.). Fill into manually operated atomization pump and bottle. An example is manufactured by Calmar-Albert GmbH, the Mistette Mark II fitted with a 16 mm high viscosity head assembly which delivers 0.2 ml./actuation.

Three individual actuations are sprayed into the mouth. Dextromethorphan is rapidly absorbed into the blood, and during spraying some portion of the sprayed liquid contacts the throat area, providing the additional benefit such as numbing of the irritated cough receptors there.

Example IV

Liquid Spray

| Item # | Material | % Comp. (w/w) |
|---|---|---|
| 1 | Dextromethorphan Base | 3.425 |
| 2 | Ethanol (100%) | 5.350 |
| 3 | Polyethylene Glycol 400 | 46.415 |
| 4 | Propylene Carbonate | 40.000 |
| 5 | Triethanolamine | 3.740 |
| 6 | Sucralose | 0.300 |
| 7 | Pro-Sweet Liquid K | 0.700 |
| 8 | Monoammonium Glycyrrhizinate | 0.050 |
| 9 | Flavorant | 0.015 |
| 10 | Colorant | 0.005 |
| | Total | 100.000 |

Add a portion of Ethanol to the active (Dextromethorphan Base) and solid sweetening agents (Sucralose, Monoammonium Glycyrrizinate) and continuously mixed at low heat (30° C.). To this vessel add the additional solvents (Propylene Carbonate, Polyethylene Glycol 400), liquid sweeteners (Pro-sweet Liquid K) and buffer (Triethanolamine, a liquid). Mix until all materials are in solution, about 2 hours time. Prepare a premix of flavorants and colorants in the remaining portion of ethanol, and add to the vessel containing the nearly completed solution. Mix until a homogenous solution is obtained, and filter through a US # 100 mesh sieve (product density=1.075 g/ml.). Fill into manually operated atomization pump and bottle. An example is manufactured by Calmer-Albert GmbE, the Mistette Mark II fitted with a 16 mm high viscosity head assembly.

Three individual actuations are sprayed into the mouth. Dextromethorphan is rapidly absorbed into the blood, and during spraying some portion of the sprayed liquid contacts the throat area, providing the additional benefit such as numbing of the irritated cough receptors there.

Example V

Liquid Centered Lozenge

| Item # | Material | % Comp. (w/w) |
|---|---|---|
| 1 | Dextromethorphan Base | 2.055 |
| 2 | Ethanol (100%) | 2.000 |
| 3 | Purified Water | 5.000 |
| 4 | Polyethylene Glycol 600 | 84.875 |
| 5 | Propylene Glycol | 5.000 |
| 6 | Sucralose | 0.300 |
| 7 | Pro-Sweet Liquid K | 0.700 |
| 8 | Monoammonium Glycyrrhizinate | 0.050 |
| 9 | Flavorant | 0.015 |
| 10 | Colorant | 0.005 |
| | Total | 100.000 |

Add a portion of Ethanol to the active (Dextromethorphan Base) and solid sweetening agents (Sucralose, Monoammonium Glycyrrizinate) and continuously mixed at low heat (30° C.). To this vessel add the additional solvents (Propylene Glycol, Polyethylene Glycol 600) and liquid sweeteners (Pro-sweet Liquid K). Mix until all materials are in solution, about 2 hours time. Prepare a premix of flavorants and colorants in the remaining portion of ethanol and water, and add to the vessel containing the nearly completed solution. Mix until a homogenous solution is obtained, and filter through a US # 100 mesh sieve (product density=1.07 g/ml.). Make individual filled lozenges containing about 1.0 ml. of liquid per lozenge by a commonly used method such as extrusion A person places a liquid filled lozenge into the mouth and sucks on the lozenge until the liquid fill is released. Some cough relief is obtained through the action of sucking on the shell of the lozenge. When the liquid center is released, dextromethorphan is rapidly absorbed into the blood.

Example VI

Liquid Centered Lozenge

| Item # | Material | % Comp. (w/w) |
|---|---|---|
| 1 | Dextromethorphan Base | 2.055 |
| 2 | Ethanol (100%) | 2.000 |
| 3 | Purified Water | 5.000 |
| 4 | Polyethylene Glycol 600 | 79.875 |
| 5 | Propylene Glycol | 5.000 |
| 6 | Sodium Glycinate | 5.000 |
| 7 | Sucralose | 0.300 |
| 8 | Pro-Sweet Liquid K | 0.700 |
| 9 | Monoammonium Glycyrrhizinate | 0.050 |
| 10 | Flavorant | 0.015 |
| 11 | Colorant | 0.005 |
| | Total | 100.000 |

Add a portion of Ethanol to the active (Dextromethorphan Base) and solid sweetening agents (Sucralose, Monoammonium Glycyrrizinate) and continuously mixed at low heat (30° C.). To this vessel add the additional solvents (Propylene Glycol, Polyethylene Glycol 600) and liquid sweeteners (Pro-sweet Liquid K). Prepare an aqueous premix of buffer (Sodium Glycinate) and add to the vessel. Mix until all materials are in solution, about 2 hours time. Prepare a premix of flavorants and colorants in the remaining portion of ethanol, and add to the vessel containing the nearly completed solution. Mix until a homogenous solution is obtained, and filter through a US # 100 mesh sieve (product density=1.07 g/ml.). Make individual filled lozenges containing about 1.0 ml. of liquid per lozenge by a commonly used method such as extrusion A person places a liquid filled lozenge into the mouth and sucks until the liquid fill is released. Some cough relief is obtained through the action of sucking on the shell of the lozenge. When the liquid center is released, dextromethorphan is rapidly absorbed into the blood, and relief from coughing is obtained within 10 minutes time.

Example VII

Liquid Elixir

| Items # | Material | % Comp. (w/w) |
|---|---|---|
| 1 | Dextromethorphan Base | 2.055 |
| 2 | Pseudoephedrine Base | 4.593 |
| 3 | Ethanol (100%) | 10.000 |
| 4 | Polyethylene Glycol 600 | 73.689 |
| 5 | Propylene Glycol | 5.000 |
| 6 | Triethanolamine | 3.740 |
| 7 | Sucralose | 0.150 |
| 8 | Pro-Sweet Liquid K | 0.700 |
| 9 | Monoammonium Glycyrrhizinate | 0.050 |
| 10 | Flavorant | 0.015 |
| 11 | Colorant | 0.005 |
|  | Total | 100 |

The composition is made according to the direction of Examples I and II.

Example VIII

Liquid Elixir

| Items # | Material | % Comp. (w/w) |
|---|---|---|
| 1 | Chlorpheniramine Base | 0.263 |
| 2 | Pseudoephedrine Base | 4.593 |
| 3 | Ethanol (100%) | 10.000 |
| 4 | Polyethylene Glycol 600 | 79.224 |
| 5 | Propylene Glycol | 5.000 |
| 6 | Sucralose | 0.150 |
| 7 | Pro-Sweet Liquid K | 0.700 |
| 8 | Monoammonium Glycyrrhizinate | 0.050 |
| 9 | Flavorant | 0.015 |
| 10 | Colorant | 0.005 |
|  | Total | 100 |

The composition is made according to the direction of Examples I and II.

Example IX

Liquid Elixir

| Items # | Material | % Comp. (w/w) |
|---|---|---|
| 1 | Acetoaminophen | 27.169 |
| 2 | Dextromethorphan Base | 1.195 |
| 2 | Pseudoephedrine Base | 2.671 |
| 3 | Ethanol (100%) | 10.000 |
| 4 | Polyethylene Glycol 1000 and PEG 600 | 25.019 |
| 5 | Polyethylene Glycol 600 | 22.765 |
| 6 | Propylene Glycol | 4.350 |

-continued

Liquid Elixir

| Items # | Material | % Comp. (w/w) |
|---|---|---|
| 7 | Polyvinyl pyrrolidone K-17PF | 2.170 |
| 8 | Triethanolamine | 3.740 |
| 9 | Sucralose | 0.150 |
| 10 | Pro-Sweet Liquid K | 0.700 |
| 11 | Monoammonium Glycyrrhizinate | 0.050 |
| 12 | Flavorant | 0.015 |
| 13 | Colorant | 0.005 |
|  | Total | 100 |

Procedure: Dissolve Dextromethorphan Base and Pseudoephedrine Base in portion ol to make a premix. In separate container heat PEG 1000, PEG 600, PVP-K17pf pylene glycol to @ 70° C. Once all material is melted and in clear liquid form add Acetoamonophen and continue to heat to 110–120° C. with continuous mixing. Remove heat once liquid is clear. Cool it to room temperature. Add the mixture to the Dextromethorphan and Pseudoephedrine premix. Also add liquid sweetener (Pro-sweet Liquid K) and buffer (Triethanolamine).

Mix until all materials are in solution. Prepare a premix of flavorants and colorants in the remaining portion of alcohol, and add to the vessel containing the nearly completed solution. Mix until homogeneous and filter through a US #100 mesh sieve. Fill in a amber glass bottles, and cap with an integrated cap/calibrated medicine dropper assembly. About 1.84 grams of the elixir is dropped onto the tongue and then swallowed. Liquid Centered Lozenge with mucosal pretreating agents in the shell.

Example X

Liquid Centered Lozenge

| Item # | Material | % Comp. (w/w) |
|---|---|---|
| 1 | Dextromethorphan Hydrobromide monohydrate | 0.690 |
| 2 | Ethanol (100%) | 10.0 |
| 3 | Purified Water | 5.0 |
| 4 | Polyethylene Glycol 600 | 74.16 |
| 5 | Propylene Glycol | 5.00 |
| 6 | Glycerine | 5.00 |
| 7 | Sucralose | 0.10 |
| 8 | Pro-Sweet Liquid K | 0.03 |
| 9 | Monoammonium Glycyrrhizinate | 0.025 |
| 10 | Flavorant | 0.015 |
| 11 | Colorant | 0.005 |
|  | Total | 100.000 |

Add a portion of Ethanol to the Dextromethorphan HBR and solid sweetening agents (Sucralose, Monoammonium glycyrrizinate) and continuously mixed at low heat (30° C.). To this vessel add the additional solvents (Propylene Glycol, Polyethylene Glycol 600, glycerine) and liquid sweeteners (Pro-sweet Liquid K). Mix until all materials are in solution, about 2 hours time. Prepare a premix of flavorants and colorants in the remaining portion of ethanol, and add to the vessel containing the nearly completed solution. Mix until a homogenous solution is obtained, and filter through a US # 100 mesh. The liquid solution is then filled into individual filled cough drops containing about 1.5 mL of liquid per drop by a commonly used method, for example, by extrusion. The candy mass of the cough drop is made to contain per drop; 5 milligrams peppermint oil, 2.5 milligrams menthol, 0.50 milligrams polysorbate 80, and 5 millligrams sodium glycinate.

A person places a liquid filled lozenge into the mouth and sucks. The mucosal tissues of the mouth are pretreated by the peppermint oil, menthol, polysorbate 80, and glycinate in the shell of the drop, so that dextromethorphan is more readily absorbed upon release of the liquid fill into the mouth. Some cough relief is obtained through the action of sucking on the shell of the lozenge. When the liquid center is released, dextromethorphan is rapidly absorbed into the blood, and relief from coughing is obtained within 10 minutes time.

Example XI

Liquid Elixir

| Item # | Material | % Comp. (w/w) |
|---|---|---|
| 1 | Dextromethorphan Hydrobromide monohydrate | 0.80 |
| 2 | Ethanol (100%) | 10.00 |
| 3 | Polyethylene Glycol 600 | 78.64 |
| 4 | Propylene Glycol | 5.00 |
| 6 | Purified water | 5.00 |
| 6 | Sucralose | 0.15 |
| 7 | Pro-Sweet Liquid K | 0.35 |
| 8 | Monoammonium Glycyrrhizinate | 0.04 |
| 9 | Flavorant | 0.015 |
| 10 | Colorant | 0.005 |
| | Total | 100.000 |

Add a portion of Ethanol to the Dextromethorphan HBR and solid sweetening agents (Sucralose, Monoammonium glycyrrizinate) and continuously mix at low heat (30° C.). To this vessel add the additional solvents (Propylene Glycol, Polyethylene Glycol 600) and liquid sweeteners (Pro-sweet Liquid K). Mix until all materials are in solution, about 2 hours time. Add the water and mix briefly. Prepare a premix of flavorants and colorants in the remaining portion of ethanol, and add to the vessel containing the nearly completed solution. Mix until a homogenous solution is obtained, and filter through a US #100 mesh. Fill into amber glass bottles and cap.

One half teaspoon (2.5 ml) is taken into the mouth and swallowed. Dextromethorphan is rapidly absorbed into the blood.

We claim:

1. An oral liquid composition comprising a pharmaceutical active including its pharmaceutically-acceptable salts, and a sweetener, in a hydrophilic, water-miscible, anhydrous solvent wherein the active in its un-ionized state has a percent solubility value in the solvent at ambient temperature that is equal to or greater than 0.075%, the active is in its un-ionized state as a monomolecular dispersion in the solvent, and wherein the active is iranamucosally delivered into the bloodstream.

2. The composition according to claim 1 wherein the pharmaceutical active has a molecular weight of less than 500 grams per mole, is capable of being ionized when the composition comprises an aqueous solvent, and has an octanol-water partition coefficient when in the unionized form of at least 100.

3. The composition according to claim 1 wherein the pharmaceutical active is in the hydrophilic, water-miscible, anhydrous solvent at a concentration less than or equal to 125% of the percent solubility value of said active.

4. The composition according to claim 3 wherein the pharmaceutical active is present in the solvent at a level from about 0.075% to about 25.0% by weight of the composition.

5. The composition according to claim 4 wherein the pharmaceutical active is present in the solvent at a level from about 0.28% to about 10.0% by weight of the composition.

6. The composition according to claim 1 wherein the hydrophilic, water-miscible, anhydrous solvent comprises from about 60% to about 99.975% by weight of the composition.

7. The composition according to claim 6 wherein the hydrophilic, water-miscible, anhydrous solvent comprises from about 70% to about 99% by weight of the composition.

8. The composition according to claim 7 wherein the hydrophilic, water-miscible, anhydrous solvent comprises from about 85% to about 98% by weight of the composition.

9. The composition according to claim 6 wherein the hydrophiliC, water-miscible. anhydrous solvent is selected from the group consisting of propylene glycol, ethanol, poly(ethylene glycol) or PEG, propylene carbonate, diethylene glycol monoethyl ether, poloxamer, glycofurol, glycerol, and mixtures thereof.

10. The composition according to claim 1 wherein the composition is in a product form of chewable capsules, liquid-filled gums, elixirs, sprays or lozenges.

11. The composition according to claim 10 wherein the product form is chewable capsules, a liquid filled gums or lozenges, wherein the chewable capsules, the liquid-filled gums, or the lozenges comprise an outer shell containing a mucosal tissue pretreatment substance and encapsulating the composition.

12. The composition according to claim 1 wherein the pharmaceutical active is an antitussive pharmaceutical active.

13. The composition according to claim 12 wherein the antitussive is selected from the group consisting of codeine, dextromethorphan, dextrorphan, diphenhydramine, hydrocodone, noscapine, oxycodone, pentoxyverine, and mixtures thereof.

14. The composition according to claim 13 wherein the antitussive is dextromethorphan.

15. The composition according to claim 13 wherein the composition further comprises an additional pharmaceutical active selected from the group consisting of antihistamines, non-sedating antihistamines, decongestants, expectorants, analgesic mucolytics, antipyretic anti-inflammatory agents, local anesthetics, and mixtures thereof.

16. The composition according to claim 15 wherein the additional pharmaceutical active is selected from the group consisting of pseudoephedrine, phenylpropylamine, acetoaminophen, chlorpheniramine, doxylamine, phenindamine, triprolidine, a salt thereof, and mixtures thereof.

* * * * *